(12) United States Patent
Plachetka

(10) Patent No.: US 6,586,458 B1
(45) Date of Patent: *Jul. 1, 2003

(54) METHODS OF TREATING HEADACHES USING 5-HT AGONISTS IN COMBINATION WITH LONG-ACTING NSAIDS

(75) Inventor: John R. Plachetka, Chapel Hill, NC (US)

(73) Assignee: Pozen Inc., Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/559,753

(22) Filed: Apr. 27, 2000

Related U.S. Application Data

(63) Continuation-in-part of application No. 09/151,912, filed on Sep. 11, 1998, now Pat. No. 6,060,499, which is a division of application No. 08/907,826, filed on Aug. 14, 1997, now Pat. No. 5,872,145, which is a continuation-in-part of application No. 09/253,278, filed on Feb. 19, 1999, now abandoned.

(60) Provisional application No. 60/024,129, filed on Aug. 16, 1996.

(51) Int. Cl.[7] ............................................. A61K 31/405
(52) U.S. Cl. ........................ 514/415; 514/449; 514/461; 514/473
(58) Field of Search ................................. 514/449, 461, 514/473, 415

(56) References Cited

U.S. PATENT DOCUMENTS

| | | | |
|---|---|---|---|
| 4,024,279 A | 5/1977 | Zor et al. | |
| 4,816,470 A | 3/1989 | Dowle et al. | 514/415 |
| 5,360,925 A | 11/1994 | Chabrier de Lassauniere et al. | 560/169 |
| 5,387,604 A | 2/1995 | McDonald et al. | 514/456 |
| 5,474,995 A * | 12/1995 | Ducharme et al. | 514/241 |
| 5,514,168 A | 5/1996 | Friedman | 607/89 |
| 5,605,917 A | 2/1997 | Ogletree | |
| 5,607,960 A | 3/1997 | Wythes | 514/414 |
| 5,618,816 A | 4/1997 | Crenshaw et al. | 514/253 |
| 5,872,145 A | 2/1999 | Plachetka | 514/415 |
| 5,942,503 A | 8/1999 | Jung et al. | 514/214 |
| 6,060,499 A * | 5/2000 | Plachetka | 514/415 |
| 6,245,802 B1 * | 6/2001 | Iyengar et al. | 514/438 |

FOREIGN PATENT DOCUMENTS

| | | | |
|---|---|---|---|
| DE | 195 42 281 | 5/1997 | |
| EP | 0 117 164 | 8/1984 | ............ A61K/9/54 |
| EP | 0 379 314 | 7/1990 | ......... C07D/471/04 |
| EP | 0 447 727 | 9/1991 | ......... C07C/311/35 |
| GB | 2 124 210 | 2/1984 | ......... C07D/209/14 |
| GB | 2 135 884 | 9/1984 | |
| GB | 2162522 | 8/1985 | |
| GB | 2 162 522 | 2/1986 | ......... C07D/209/14 |
| WO | WO 97/38986 | 10/1997 | ......... C07D/261/08 |
| WO | WO 98/06392 | 2/1998 | ......... A61K/31/405 |
| WO | WO 98/15275 | 4/1998 | ......... A61K/31/485 |
| WO | WO 98/20870 | 5/1998 | ......... A61K/31/165 |
| WO | WO 99/45905 | 9/1999 | |
| WO | WO 00/25779 | 5/2000 | |

OTHER PUBLICATIONS

Certified Translation of AF1 above.

Anderson, et al., "Double–Blind Study of Naproxen vs Placebo in the Treatment of Acute Migraine Attacks," *Cephalalgia* 9:29–32 (1989).

Baumel, "Migraine: A Pharmacologic Review with Newer Options and Delivery Modalities," *Neurology* 44:S13–S17 (1994).

Bolten, "Scientific Rationale for Specific Inhibition of COX–2," *J. Rheumatol.* 25:2–7 (1998).

Boureau, et al., "Comparison of Subcutaneous Sumatriptan with Usual Acute Treatmens for Migraine," *Eur. Neurol.* 35:264–269 (1995).

Bousser, et al., "Combined Low–Dose Acetylsalicylic Acid and Dihydroergotamine in Migraine Prophylaxis," *Cephalalgia* 8:187–102 (1988).

Bousser, et al., "Efficacy of Subcutaneous Sumatriptan in the Acute Treatment of Early–Morning Migraine: A Placebo–Controlled Trial," *J. Intern. Med.* 234:211–216 (1993).

Cady, et al., "Treatment of Acute Migraine with Subcutaneous Sumatriptan," *JAMA* 265:2831–2835 (1991).

Cady, et al., "Efficacy of Subcutaneous Sumatriptan in Repeated Episodes of Migraine," *Neurology* 43:1363–1368 (1993).

Capobianco, et al., "An Overview of the Diagnosis and Pharmacologic Treatment of Migraine," *Mayo Clin. Proc.* 71:1055–1066 (1996).

Centonze, et al., "Evaluation of the Efficacy of Oral Sumatriptan in the Management of Migraine Attacks, Clinical Results," *La Clinica Teraputica* 146:721–728 (1995). (Article in Italian English Abstract).

Dahlöf, "How Does Sumatriptan Perform in Clinical Practice," *Caphalalgia* 15:21–28 (1995).

Dechant, et al., "Sumatriptan—A Review of Its Pharmacodynamic and Pharmacokinetic Properties, and Therapeutic Efficacy in the Acute Teatment of Migraine and Cluster Headache," *Drugs* 43:776–798 (1992).

Demarin, et al., "Pharmacotherapy of Migraine," *Acta Clin. Croat.* 34:81–89 (1995).

(List continued on next page.)

Primary Examiner—Dwayne C. Jones
Assistant Examiner—C. Delacroix-Muirheid
(74) Attorney, Agent, or Firm—Michael A. Sanzo; Fitch, Even, Tabin & Flannery

(57) ABSTRACT

The invention is directed to methods and compositions that can be used in the treatment of headaches. In particular, methods and compositions are described involving the combination of a long-acting NSAID and a 5-HT agonist. Included among the long-acting NSAIDs are cyclooxygenase-2 inhibitors.

32 Claims, No Drawings

OTHER PUBLICATIONS

Donnelly, et al., "Review Article: COX–II Inhibitors—a New Generation of Safer NSAIDs?," *Aliment. Pharmacol. Ther.11*:227–236 (1997).
Furlong, et al., "Prescribing Practices for the Management of Headache in Newfoundland and Labrador," *Headache 36*:542–546 (1996).
Furst, "Meloxicam: Selective COX–2 Inhibition in Clinical Practice," *Semin. Arthritis Rheum. 26*:21–27 (1997).
Grazzi, et al., "A Review of the Treatment of Primary Headaches. Part I:Migraine," *Intl. J. Neurol. Sci. 16*:577–586 (1995).
Griswold, et al., "Constitutive Cyclooxygenase (COX–1) and Inducible Cyclooxygenase (DOX–2): Rationale for Selective Inhibition and Progress to Date," *Med. Res. Rev. 16*:181–206 (1996).
Hoernecke, et al., "Treatment of Migraine Attacks: Combination of Dihydroergotamine Tartrate and Paracetamol in Comparison with Individual Drugs and Placebo," *Medizinische Klink 88*:642–648 (1993); Abstract from Medline Online, Database Accession No. NLM8295604.
Klapper, "The Pharmacologic Treatment of Acute Migraine Headaches," *J. Pain Symptom Manage. 8*:140–147 (1993).
Klapper, "Toward a Standard Drug Formulary for the Treatment of Headache," *Headache 35*:225–227 (1995).
Kumar, "Recent Advances in the Acute Management of Migraine and Cluster Headaches," *J. Gen. Internal Med. 9*:339–348 (1994).
Krymchantowski, et al., "Tolfenamic Acid Decreases Migraine Recurrence When Used with Sumatriptan," *Cephalalgia 19*:186–187 (1999).
Krymchantowski, et al., "Naproxen Sodium Decreases Migraine Recurrence When Used with Sumatriptan," *Cephalalgia 19*:357–358 (1999).
Lance, "Headache," *Ann. Neurol. 10*:1–10 (1981).
Lane, "Pain Management in Osteoarthritis: The Role of COX–2 Inhibitors," *J. Rheumatol. 24*:20–24 (1997).
Lipsky, et al., "Outcome of Specific COX–2 Inhibition in Rheumatoid Arthritis," *J. Rheumatol 24*:9–14 (1997).
Matthew, "Cyclical Propylactic Treatment of Menstrual Migraine Using Naproxen and Ergotamine," *Headache 26*:314 (1986).
Matthew, et al., "Advances in Migraine Drug Therapy," *Drug Therapy 23*:37–48 (1993).
Moskowitz, et al., "Neuroeffector Functions of Sensory Fibers: Implications for Headache Mechanisms and Drug Actions," *J. Neurol. 238*:S–18–S22 (1991).
Oral Sumatriptan Group, "Sumatriptan—An Oral Dose–Defining Study," *Eur. Neurol. 31*:300–305 (1991).
Parma, et al., "II Trattamento dell'Emicrania: Uno Studio Nella Medicina Generale," *Ricerca & Pratica 11*:64–7 (1995) in Italian.
Translation of AK5 above: Parma, et al., "The Treatment of Migraine: A Study in General Medicine," *Ricerca & Pratica 11*:64–72 (1995).
Peroutka, "Beyond Monotherapy: Rational Polytherapy in Migraine," *Headache 38*:18–22 (1998).
Pfaffenrath, et al., "Efficacy and Safety of Sumatriptan Tablets (25 mg, 50 mg, and 100 mg) in the Acute Treatment of Migraine: Defining the Optimum Doses of Oral Sumatriptan," *Headache 38*:184–190 (1998).
Plosker, et al., "Sumatriptan: A Reappraisal of Its Pharmacology and Therapeutic Efficacy in the Acute Treatment of Migraine and Cluster Headache," *Drugs 47*:622–651 (1994).
Pradalier, et al., "La Migraine Cataméniale," *Contracept. Fertil. sex. 23*:361–365 (1995) in French.

Translation of AP5 above: Pradalier. et al., "Menstrual Migraine," *Contracept. Fertil. Sex. 23*:361–365 (1995).
Rac. et al., "Formulation of Antimigraine Mixtures," STN HCA: vol. 8 (1994), abstract — XP–002078672.
Saadah, "Abortive Migraine Therapy with Oral Naproxen Sodium Plus Metoclopramide Plus Ergotamine Tartrate with Caffeine," *Headach 32*:95–97 (1992).
Sharma, et al., "An Update on Eicosanoids and Inhibitors of Cyclooxygenase Enzyme Systems," *Indian J. Exper. Biol. 35*:1025–1031 (1997).
Sheftell, et al., "Subcutaneous Sumatriptan in a Clinical Setting: The First 100 Consecutive Patients with Acute Migraine in a Tertiary Care Center," *Headache 34*:67–72 (1994).
Silberstein, "Treatment of the Migraine Attack," *Curr. Opn. Neorol. 7*:258–263 (1994).
Solomon, "Therapeutic Advances in Migraine," *J. Clin. Pharmacol. 33*:200–209 (1993).
Thomson, "A Study to Compare with Oral Sumatriptan with Oral Aspirin plus Oral Metoclopramide in the Acute Treatment of Migraine," *Eur. Neurol. 32*:177–184 (1992).
Todd, et al., "Naproxen: A Reappraisal of Its Pharmacology, and Therapeutic Use in Rheumatic Diseases and Pain States," *Drugs 40*:91–137 (1990).
Tokola, et al., "Effects of Migraine Attack and Metoclopramide on the Absorption of Tolfenamic Acid," *Br. J. Clin. Pharmac. 17*:67–75 (1984).
Tokola, et al., "Tolfenamic Acid, Metroclopramide, Caffeine and their Combinations in the Treatment of Migraine Attacks," *Cephalalgia 4*:253–263 (1984).
Von Seggern, et al., "Cost Considerations in Headache Treatment Part 2: Acute Migraine Treatment," *Headache 36*:493–502 (1996).
Welch, "Drug Therapy of Migraine," *N. E. J. Med. 329*:1476–1483 (1993).
Wilkinson, et al. "Migraine Cluster Headache—their Management with Sumatriptan: A Critical Review of the Current Clinical Experience," *Cephalalgia 15*:337–357 (1995).
Wittig, "Renal Papillary Necrosis Following Emergency Department Treatment of Migraine," *J. Emer. Med. 14*:373–376 (1996).
Schuller, et al., "Recurrent Headaches: What Every Allergist Should Know," *Ann. Allergy Asthma Immunol. 76*:219–230 (1996).
Krymchantowski et al., "Tolfenamic acid decreases migraine recurrence when used with sumatriptan," *Cephalgia 19*:186–187 (1999).
Haag, "Kombianalgetika in der Kopfschmerz–therapie," *Duetsche Apotheker Zeitung, De Deutscher Apotheker Zeitung 4*:43–48 (1993) Stuttgart.
Dialog abstract of German patent document DE 195 42 281 (listed as document AK2), Derwent World Patents Index accession number 1997–281994/199726.
Myllylä, et al., "Tolfenamic Acid Rapid Release Versus Sumatriptan in the Acute Treatment of Migraine: Comparable Effect in a Double–Blind, Randomized, Parallel–Group Study," *Headache 38(3)*:201–207 (1998).
Pavel, et al., "Formulation of Antimigraine Mixtures," STN HCA 8 (1994), Abstract XP–002078672.
Abstracts of Talley, et al., O.D. Searle Celebrix Registry 169590–42–5, "Celebrex," SC58635, patents for migraine headache: 5,466,823 (11/95); 5,504,215 (4/96); 5,508,426 (4/96); 5,510,496 (4/96); 5,516,907 (5/96); 5,521,207 (5/96); 5,563,165 (10/96); 5,700,816 (12/97); 5,753,688 (5/98); 5,760,068 (6/98); and 5,932,598 (8/99).
International Search Report for PCT/US00/03897.

* cited by examiner

METHODS OF TREATING HEADACHES USING 5-HT AGONISTS IN COMBINATION WITH LONG-ACTING NSAIDS

CROSS REFERENCE TO RELATED APPLICATIONS

The present application is a continuation-in-part of U.S. Ser. No. 09/151,912, filed Sep. 11, 1998 now U.S. Pat. No. 6,060,499. The '912 application is a division of U.S. Ser. No. 08/907,826, filed Aug. 14, 1997 (now U.S. Pat. No. 5,872, 145) which claims priority to U.S. provisional application No. 60/024,129, filed on Aug. 16, 1996 (now abandoned). Which is a CIP to U.S. Ser. No. 09/253,278, filed Feb. 19, 1999 now abandoned.

FIELD OF THE INVENTION

The invention is directed to methods of treating patients for headache by administering compositions containing a 5-HT agonist and a long-acting NSAID. Among the preferred long-acting NSAIDs are cyclooxygenase-2 inhibitors (COX-2 inhibitors).

BACKGROUND OF THE INVENTION 5-hydroxytryptamine (5-HT or 5HT), also known as serotonin or enteramine, is a vasoactive agent and an endogenous neurotransmitter. It acts on receptors found in the central and peripheral nervous system as well as on blood vessels. Other drugs acting at these receptor sites are known as 5-HT agonists or antagonists. The 5-HT receptors have been divided into several sub-classes, some of which themselves contain subtypes. Examples of subtypes of serotonin receptors are 5-HT1, 5-HT1-like, $5\text{-HT1}_B$, $5\text{-HT1}_D$, 5-HT2, 5-HT3, etc.

5-HT1-like agonists and agonists acting at other 5-HT1 sites make up a group of therapeutics that may be used for the treatment of migraine headache. A representative member of this group is sumatriptan succinate (distributed under the name Imitrex™ by Glaxo Wellcome, and described in U.S. Pat. No. 4,816,470). Ergot alkaloids and related compounds are also known to have 5-HT agonist activity and have been used in migraine therapy. Included among these compounds are ergotamine tartrate, ergonovine maleate, and ergoloid mesylates (e.g., dihydroergocornine, dihydroergocristine, dihydroergocryptine, and dihydroergotamine mesylate (DHE 45)). Unfortunately, it has been reported that of the 50 to 70% of patients who experience migraine symptom relief within two hours after receiving a 5-HT agonist, 30–50% experience migraine symptoms again within the next 24 hours. These subsequent headaches are typically termed "rebound," "relapse," "recurrent" or "secondary" headaches.

A variety of analgesics have also been administered to migraine patients. For example, K. M. A. Welch (*New Eng. J. Med.* 329:1476–1483 (1993)) sets forth the following dosages of analgesics as being useful: aspirin, 500–650 mg; acetaminophen, 500 mg; naproxen sodium, 750–825 mg; tolfenamic acid, 200–400 mg; and ibuprofen, 200 mg. However, like the 5-HT agonists, these agents, when taken alone, are rarely effective in providing complete relief symptoms and, after initial remission, migraine symptoms often return.

The problems that occur with migraine headaches may also be present in other types of headache as well. In all cases, an ideal therapy would reduce or eliminate the symptoms associated with the initial attack and minimize the frequency of later recurrences.

RELATED ART

The following studies provide background information that should aid in understanding the present invention.
1. Plosker, et al., *Drugs* 47:622–655 (1994).
2. Sheftel, et al., *Headache* 34:67–72 (1994).
3. Wilkinson, et al., *Cephalalgia* 15:337–357 (1995).
4. Silberstein, S D, *Curr. Opin. Neurol.* 7:258–263 (1994).
5. Welch, K. M. A., *New Eng. J. Med.* 329:1476–1483 (1993).
6. Kumar, K. L., *J. Gen. Int. Med.* 9:339–348 (1994).

SUMMARY OF THE INVENTION

The present invention is based upon the discovery that co-administration of a 5-HT agonist together with a long-acting, non-steroidal anti-inflammatory drug (LA-NSAID) represents an improved treatment for a wide variety of headaches. Compared to the administration of either drug alone, the combination produces longer lasting efficacy and a substantial reduction in the frequency relapse of headaches. As used herein, the term "longer lasting efficacy" means that drugs produce relief from symptoms associated with a headache for a longer period of time.

In its first aspect, the invention is directed to a method of treating a patient for headache by administering a 5-HT agonist together with a long-acting, non-steroidal anti-inflammatory drug. These two agents should be concomitantly administered, i.e., they should be given in close enough temporal proximity to allow their individual therapeutic effects to overlap. The amount of 5-HT agonist and LA-NSAID administered should be sufficient to reduce the frequency of headache relapse in patients or produce longer lasting efficacy compared to the administration of either one of these agents in the absence of the other. This procedure may be used to treat headaches falling into any of a wide variety of classes including: migraine headache; tension-type headache; cluster headache and chronic paroxysmal hemicrania; miscellaneous headache unassociated with a structural lesion; headache associated with a non-vascular intracranial disorder; headache associated with the administration of a substance or its withdrawal; headache associated with noncephalic infection; headache associated with a metabolic disorder; headache associated with a disorder of the cranium, neck, eyes, ears, nose, sinuses, teeth, mouth or other facial or cranial structure; cranial neuralgias; and nerve trunk pain and deafferentiation pain. (For a description of classes, see Olesen, et al., *The Headaches*, pp. 9–14, Raven Press; see also, "Classification and diagnostic criteria for headache disorders, cranial neuralgias and facial pain," Headache Classification Committee of the International Headache Society, *Cephalalgia* 8(supp. 7):1–96 (1988)).

The invention is also directed to a pharmaceutical composition in unit dose form that is useful in treating headache patients and which contains a 5-HT agonist and a long-acting, non-steroidal, anti-inflammatory drug. The two therapeutic agents, i.e., the 5-HT agonist and LA-NSAID, should be present in amounts such that, upon administration of one or more unit doses of the composition, a patient experiences longer lasting efficacy than with the administration of either agent alone. The composition may be included as part of a therapeutic package in which one or more unit doses are placed in a finished pharmaceutical container. Labeling may be included to provide directions for using the composition in the treatment of headache.

The methods and compositions discussed above are compatible with any dosage form or route of administration. Thus, agents may be administered orally, intranasally, rectally, sublingually, buccally, parenterally, or transdermally. Dosage forms may include tablets (including quick dissolve tablets), trochees, capsules, caplets, dragees, lozenges, parenterals, liquids, powders, and formulations designed for implantation or administration to the surface of the skin. Optionally, these dosage forms may be coordinated or designed for the slow release of therapeutic agents. They can be prepared using methods that are standard in the art and may include additional therapeutic agents, e.g., one or more additional analgesics.

Preferred 5-HT agonists for use in methods and compositions include sumatriptan, eletriptan, rizatriptan, frovatriptan, almotriptan, zolmitriptan, and naratriptan. The most preferred 5-HT agonist is sumatriptan which may be administered in a dosage from about 0.01 to about 300 mg. When administered non-parenterally, the typical dosage of sumatriptan is from about 25 to about 100 mg with about 50 mg being generally preferred and, when administered parenterally, the preferred dosage is about 6 mg. However, these dosages may be varied according to methods standard in the art so that they are optimized for a particular patient or for a particular combination of sumatriptan and long-acting NSAID. For example, effective dosage forms containing naproxen may have more than 100 mg of sumatriptan.

Among the preferred long-acting NSAIDs for use in compositions and methods are: naproxen, flurbiprofen, ketoprofen, oxaprozin, etodolac, indomethacin, ketorolac, nabumetone, mefanamic acid, and piroxican. Of these, the most preferred is naproxen or a pharmaceutically acceptable salt of naproxen. This should be administered to patients and present in a unit dosage of a composition in an amount of greater than 200 mg and preferably between 200 mg and 600 mg. One particularly preferred composition contains sumatriptan in an amount of greater than 25 mg and naproxen in an amount of greater than 200 mg. Although not essential, it is expected that the sodium salt of naproxen will generally be used.

A second group of preferred long-acting NSAIDs for use with any of the above compositions and methods are the cyclooxygenase-2 (COX-2) inhibitors. Members of this group include: celecoxib; rofecoxib; meloxicam; JTE-522; L-745,337; NS398; and pharmaceutically acceptable salts thereof. The most preferred is celecoxib in an amount of between 50 and 500 mg. Any of the 5-HT agonists discussed above may be used in combination with the COX-2 inhibitors with sumatriptan being preferred. For example, a method or composition may utilize a dosage of 5 to 100 mg of sumatriptan and 100 to 400 mg celecoxib.

The COX-2 inhibitors may be especially useful in the treatment of migraine headaches. Thus, the invention includes a method of treating a migraine patient by administering a 5-HT agonist in combination with a COX-2 inhibitor. These agents should be given concomitantly and should be delivered in an amount sufficient to reduce migraine relapse or produce longer lasting efficacy relative to the effect of either agent alone. The invention also includes pharmaceutical compositions in unit dose form which are designed for treating migraine patients and which contain these agents, i.e., a 5-HT agonist and a COX-2 inhibitor. The compositions may be included as part of a therapeutic package in which one or more unit doses are placed in a finished pharmaceutical container. The package may include labeling directing the use of the composition in the treatment of migraine.

The dosage forms and routes of administration discussed previously are all compatible with the COX-2 methods and compositions. The most preferred 5-HT agonist is sumatriptan at 50 mg when used orally and at about 6 mg when used parenterally. Other 5-HT agonists that may be used include: eletriptan, rizatriptan, frovatriptan, almotriptan, zolmitriptan and naratriptan. If desired, other therapeutic agents, e.g., one or more additional analgesics, may be included in the compositions or methods.

The preferred COX-2 inhibitor is celecoxib, typically at 50–500 mg per unit dose. Especially preferred are methods and compositions utilizing 5 to 100 mg of sumatriptan and 100 to 400 mg celecoxib. If desired, one or more additional therapeutic agents, e.g., an additional analgesic, may be included. Finally, the 5-HT agonist, the COX-2 inhibitor, or both, may, if desired, be used in sub-MED amounts.

DETAILED DESCRIPTION OF THE INVENTION

It has been discovered that a combination therapy of a 5-HT agonist, including drugs structurally similar to sumatriptan or members of the ergot family of compounds, combined with a long acting nonsteroidal anti-flammatory drug (LA-NSAID) substantially reduces or eliminates relapse in a significant portion of headache patients that experience this phenomenon. The combination results in an enhanced therapeutic effect allowing for greater efficacy and/or lower doses than can be obtained with the conventional doses of either individual agent. Naproxen sodium is one such long acting NSAID and sumatriptan is one such 5-HT agonist. The invention will best be understood with reference to the following definitions:

A. "Long acting" in relation to NSAIDs shall mean a pharmacokinetic half-life of at least 2 hours, preferably at least 4 hours and more preferably at least 8–14 hours and a duration of action equal to or exceeding about 6–8 hours. Examples of appropriate NSAIDs are: flurbiprofen with a half-life of about 6 hours; ketoprofen with a half-life of about 2 to 4 hours; naproxen and naproxen sodium with half-lives of about 12 to 15 hours and about 12 to 13 hours respectively; oxaprozin with a half-life of about 42 to 50 hours; etodolac with a half-life of about 7 hours; indomethacin with a half-life of about 4 to 6 hours; ketorolac with a half-life of up to about 8–9 hours; nabumetone with a half-life of about 22 to 30 hours; mefenamic acid with a half-life of up to about 4 hours; and piroxicam with a half-life about of about 4 to 6 hours. If an analgesic does not naturally have a half life sufficient to be long-acting, it can be made long-acting by the way in which it is formulated. Unless otherwise indicated, the term "long-acting NSAID" shall include NSAIDs (e.g., aspirin) specially formulated to be long-acting. For the purposes of the present invention, the term shall also include acetaminophen formulated to be long-acting. Methods for making appropriate long-acting formulations are well known in the art (see e.g., *Remington's Pharmaceutical Sciences*, 16$^{th}$ ed., A. Oslo editor, Easton, Pa. (1980); *Controlled Drug Delivery*, Edith Mathiowitz, John Wiley & Sons (1999), ISBN: 0471148288).

B. "Therapeutically effective amount" as to drug dosage shall mean a dosage that provides the specific pharmacological response for which the drug is administered in a significant number of subjects in need of such treatment. It is emphasized that headaches are not well understood and the etiologies of particular headaches will vary, as does the response to particular drugs. Thus, reference to "specific pharmacological response for which the drug is administered in a significant number of subjects in need of such treatment" is a recognition that a "therapeutically effective amount," administered to a particular subject in a particular instance may not abort the onset of a headache or relieve headache pain, even though such dosage is deemed a "therapeutically effective amount" by those skilled in the art. It is to be further understood that drug dosages are, in particular instances, measured as oral, or parenteral or inhaled dosages or with reference to drug levels as measured in blood.

For 5-HT agonists, NSAIDs and non-NSAID analgesics (particularly with respect to those already on the market) a therapeutically effective amount shall include (but not be limited to) the dosage that has been determined as safe and effective for any indication. Nevertheless, in particular applications this does not exclude substantially lesser (or greater) dosages than established minimum (or maximum) dosages for which a particular 5-HT agonist or NSAID could be used to effectively treat an episode of headache. Particular reference is made to the following dosages of 5-HT agonists and NSAIDs, any of which may be combined into single dosage forms.

Sumatriptan is usefully provided as oral tablets of 25 mg, 50 mg and 100 mg and as a parenteral dosage form containing about 6 mg/ml and about 6 mg/0.5 ml for subcutaneous administration. Oral doses of about 1–300 mg are also useful with particular reference to doses of about 10–100 mg. Peak serum concentrations of approximately 1–300 ng/ml are produced with doses in these ranges. Subcutaneous injections of about 1 to 8 mg of sumatriptan are useful, with particular reference to about 3 to 6 mg doses. Injections produce peak serum concentrations of approximately 1 to 150 ng/ml. Other dosage forms of sumatriptan include, but are not limited to, suppositories, aerosols for inhalation or intranasal administration, and nose drops, all of which may be used in the practice of this invention.

Ergotamine tartrate in oral doses of about 1 to 5 mg with particular reference to about 1–2 mg are useful, as are doses of about 1–2 mg at 30 minute intervals, up to about 6 to 8 mg in one day. Oral inhalation of sequential doses of about 0.1 to 0.5 mg at intervals of about 5 minutes are noted, with particular reference to doses of about 0.36 mg. Suppositories of 0.1 to 5 mg with particular reference to about 2 mg are useful.

Ergonovine maleate may be administered by injection of about 0.2 mg/ml, and oral tablets of about the same strength may also be given.

Ergoloid mesylates (i.e. dihydroergocornine, dihydroergocristine, dihydroergocryptine (dihydro-α-ergocryptine and dihydro-β-ergocryptine) are usefully provided in tablets of from about 0.2 to 2.5 mg with particular reference to about 0.5 to about 1.0 mg tablets. Such tablets contain about 0.167 mg of each of dihydroergocornine, dihydroergocristine, and dihydroergocryptine (dihydro-α-ergocryptine and dihydro-β-ergocryptine). Liquid suspension and liquid filled capsules of about 1 mg/ml are also useful.

With respect to NSAIDs, it is expected that the skilled practitioner will adjust dosages on a case by case basis using methods well established in clinical medicine. Nevertheless, the following general guidelines may be of help. Indomethacin is particularly useful when contained in tablets of from about 25 to 75 mg, in suppositories of about 50 mg, and in oral suspensions of about 25 mg/5 ml. A typical daily oral dosage of indomethacin is three 25 mg doses taken at intervals during one day, amounting to 75 mg total. However, daily doses of up to about 150 mg are useful in some subjects. Sustained release dosage forms of indomethacin are also available and provide longer lasting blood levels than conventional tablets. In particular, a 75 mg sustained release dosage form can be used as an alternative to 25 mg three times daily or 75 mg twice daily can be substituted for 50 mg three times daily.

Ibuprofen is conveniently provided in tablets or caplets of 50, 100, 200, 300, 400, 600 and 800 mg and as a suspension of 100 mg/5 ml. Daily doses should not exceed 3200 mg and doses should be individualized. In addition, 200 mg–800 mg may be particularly useful when given 3–4 times daily.

Flurbiprofen is particularly useful when contained in tablets of from about 50 to 100 mg. Daily doses of about 100 to 500 mg, and particularly about 200 to 300 mg total are useful.

Ketoprofen is particularly useful when contained in capsules of from about 25 to 75 mg. Daily doses of about 100 to 500 mg, and particularly about 100 to 300 mg are useful, as is about 25 to about 50 mg every six to eight hours.

Naproxen is particularly useful when contained in tablets of from about 250 to about 500 mg and in oral suspensions of about 125 mg/5 ml. For naproxen sodium, tablets of about 275 or about 550 mg are particularly useful. Initial doses of about 100 to 1250 mg, and particularly 350 to 800 mg are also useful with particular note of doses of about 550 mg.

Oxaprozin has a pharmacokinetic half-life of 42–50 hours and a bioavailability of 95%. It is usefully provided as caplets of 600 mg. Daily doses of 1200 mg have been found to be particularly useful and should not exceed 180 mg or 26 mg/kg. The lowest effective dose should always be used.

Etodolac is usefully provided in capsules of 200 mg and 300 mg or in tablets of 400 mg. Useful doses for acute pain are 200–400 mg every 6–8 hours, not to exceed 1200 mg/day. Patients <60 kg are advised not to exceed doses of 20 mg/kg. Amounts for other uses are also limited to 1200 mg per day, preferably in divided doses, e.g., 2, 3, or 4 times daily.

Ketorolac is usefully provided in tablets of 10 mg and as a sterile parenteral preparation for injection in 15 mg/ml and 30 mg/ml dosage forms. Oral doses of up to 40 mg with particular reference to 10–30 mg per day and parenteral doses up to 120–150 mg per day have been useful in the amelioration of pain.

Nabumetone is usefully provided in tablets of 500 mg and 750 mg. Daily doses of up to 1500–2000 mg/day after an initial dose of 1000 mg are of particular use.

Mefenamic acid is particularly useful when contained in capsules of from about 250 mg. For acute pain such as migraine, an initial dosage of about 100 to 1000 mg and particularly about 500 mg is useful, though other dosages may be required for specific subjects.

Meclofenamate sodium is usefully provided as capsules of 50 mg and 100 mg. Daily doses up to 400 mg are useful, particularly in individual doses of 50–100 mg every 4–6 hours.

Piroxicam is particularly useful when in tablets of from about 10 to 20 mg. It is noted that, as steady state plasma concentrations are not reached until about 7 to 12 days of dosing, prophylactic use of piroxicam is a specific avenue of therapy to establish a plasma concentration of greater than about 5 to 6 $\mu$g/ml. In such a situation, coordination and co-timely administration of a 5-HT agonist is achieved by the administration of the 5-HT agonist approximately at the onset of a migraine attack.

Celecoxib (Celebrex®) is particularly useful when contained in tablets of from about 100 to 200 mg. Recommended dosages are typically 100 mg twice per day or 200 mg once per day. A sub-med amount of celecoxib is less than about 150 mg per day and particularly less than about 100 mg per day, e.g., about 75 mg per day or 50 mg per day (see, Bolten, J., *Rheumatolog. Suppl.*, 51:2–7 (May, 1998)). Celecoxib peak plasma concentrations occur approximately 3 hours after oral dosing. The effective half-life is approximately 11 hours. In one embodiment, coordination and co-timely administration of a 5-HT agonist is achieved by the administration of the 5-HT agonist approximately at the onset of a migraine.

Rofecoxib (Vioxx®) for oral administration is available in tablets of 12.5, 25 or 50 mg and in an oral suspension containing either 12.5 mg or 25 mg rofecoxib per 5 ml. The recommended initial daily dosage for the management of acute pain is 50 mg. Peak plasma concentrations of rofecoxib typically occur about 2–3 hours after oral administration and the drug has a half life of about 17 hours.

Without being bound by any theory, it is believed that the GI and renal toxicity associated with use of NSAIDs is the result of COX-1 inhibition, stemming from a reduction in the protective prostaglandins that preserve the integrity of the stomach lining and maintain normal renal function. Likewise, anti-inflammatory effects are largely due to inhibition of COX-2 and the resultant decreases in pro-inflammatory prostaglandins, like thromboxane. Drugs which selectively inhibit the COX-2 isozyme, like celecoxib, rofecoxib, meloxicam, piroxicam, JTE-522 and L-745,337, produce analgesia and reduce inflammation without removing the protective prostaglandins in the stomach and kidney.

In certain embodiments, selective inhibition of the COX-2 isozyme provides a beneficial therapeutic profile in the treatment of headaches, particularly migraine headaches. While the precise etiology of migraine remains unknown, the intense head pain is thought to result from sensitization and neurogenic inflammation at the trigeminal sensory nerve terminals which enervate cerebral blood vessels. NSAIDs have been shown to alleviate migraine headache pain, probably through a combination of their analgesic and anti-inflammatory properties. In the practice of the present invention, selective inhibitors of COX-2 (which have little effect on COX-1) produce similar effects, based on the preservation of prostacyclin levels, while being better tolerated in terms of potential GI and renal toxicity, and this effect is not negated in combination with 5-HT agonists. Additional information on COX-2 inhibitors may be found in the following references:

1. Sharma-S, et al., *Indian J. Exp. Biol.* 35:1025–31 (1997).
2. Lane, *J. Rheumatol* 24 (Suppl 49):20–4 (1997).
3. Lipsky, et al., *J. Rheumatol.* 24 (*Suppl* 49):9–14 (1997).
4. Furst, *Semin. Arthritis. Rheum* 26 (6 *Suppl* 1):21–7 (1997). Note particularly the dosage range of meloxicam at about 7.5 mg per day or more, and including 15 mg per day in arthritis pain indications.
5. Donnelly et al., *Aliment-Pharmacol-Ther.* 11(2):227–36 (1997).
6. Griswold, et al., *Med. Res. Rev.* 16(2): 181–206 (1996).

C. "Co-timely" with respect to drug administration means administration of a second drug for headache symptom relief while a first drug is still present in a therapeutically effective amount. It is to be understood that in some instances this will require sequential administration. Alternatively, multiple routes of administration may be employed, e.g., intravenous or subcutaneous injection of a 5-HT agonist may be combined with oral administration of a long acting NSAID.

D. "Coordinated" in the practice of the present invention means administration of an NSAID in such a manner that effective plasma levels of the NSAID are present in a subject from about one hour to about 12–24 hours after the onset of migraine or onset of precursor symptoms of a migraine. In some embodiments, this will be about 1 to 12 hours after a 5-HT agonist has been administered. The coordination time is clearly related to the route of NSAID administration. For example, intramuscular routes will generally have shorter lead times to peak plasma levels for particular NSAIDs as follows: flurbiprofen peaks in about 1 to 2 hours; ketoprofen peaks in about one-half to 2 hours; naproxen and naproxen sodium peak at about 2 to 4 hours and 1 to 2 hours respectively; oxaprozin peaks at about 3 to 5 hours; etodolac peaks at about 1 to 2 hours; indomethacin peaks at about 1 to 4 hours; ketorolac peaks about one-half to 1 hour; nabumetone peaks at about 2.5 to 4 hours; mefenamic peaks at about 2 to 4 hours; meclofenamate peaks in 0.5–1 hours; and piroxicam peaks at about 3 to 5 hours.

E. "5-HT agonist" is to be broadly understood to encompass 5-HT agonists of all types, including but not limited to 5 HT1-like agonists, 5-HT1B, and 5 HT1D agonists. Particular reference is made to sumatriptan succinate and related 5-HT agonist heterocyclic compounds described in U.S. Pat. No. 4,816,470; ergot alkaloids and related compounds such as dihydroergotamine mesylate (DHE 45), ergotamine tartrate, ergonovine maleate, ergoloid mesylates, i.e. dihydroergocornine, dihydroergocristine, dihydroergocryptine (dihydro-α-ergocryptine and dihydro-β-ergorcryptine); eletriptan as described in European Patent Application 379314; Allelix ALX 1323; rizatriptan; frovatriptan; and almotriptan; and naratriptan.

F. "Relapse headaches" variously and interchangeably termed "rebound," "relapse," "recurrent" or "secondary" headaches occur when people experiencing initial symptom relief (or avoidance of migraine in the case of treated precursor symptoms) upon administration of a therapeutic agent, experience a return of headache or other related symptoms within the next 24 hours.

"Rebound moderated" as to sumatriptan shall mean that at least about 20% of people that ordinarily experience relapse do not experience recurrence of headaches within the 24 hours subsequent to "initial relief" as defined below. As to ergots, rebound moderated shall mean a statistically significant improvement with respect to return of headaches or related symptoms.

G. "Initial migraine relief" shall be understood to be the reduction or abolition of symptoms from first onset of either a migraine attack or the precursor indicia of a migraine headache such as the aura and visual "scotoma" in about a 24 hour period.

H. "Unit dosage from" shall mean a single drug administration entity. By way of example, a single tablet, capsule, dragee, or trochee, suppository, or syringe combining both a 5-HT agonist and an NSAID would be a unit dosage form. Administration of a unit dosage form will result in blood levels of the NSAID required to produce a therapeutic effect within about the first hour after dosing and will still be present at least about 8–12 hours after initial dosing, and in particular instances, for as long as about 24 hours after dosing. Blood levels of the 5-HT agonist normally associated with a therapeutic effect will be present within the first hour and should persist in measurable quantities for at least about 4–6 hours. In the particular example of the NSAID naproxen sodium, about 550 mg combined with the 5-HT agonist sumatriptan (about 25 mg), results in blood levels of naproxen of 40 mcg/ml within 1 hour after dosing and blood levels exceeding 20 mcg/ml at about 12 hours after dosing. Blood levels of sumatriptan will be approximately 10 mcg/ ml within the first hour after dosing and will remain in measurable quantities for at least about 4–6 hours.

Other combinations of NSAIDs and 5-HT agonists likewise provide effective blood levels over the time periods specified above. It is preferred that the dosage form provide blood levels consistent with rapid initial headache or migraine relief and a reduced incidence of relapse headache.

I. "Quick dissolve" in reference to a tablet or other oral dosage form shall mean that the oral dosage form is at least 95% dissolved within 20 minutes after administration. In determining "quick dissolve," reference is made to standard USP test methodology.

J. "Enhanced therapeutic effect" in the context of the present invention means that the initial relief of migraine symptoms occurs more quickly with a claimed combination of two agents compared to the same doses of each component given alone; or that doses of one or both component(s) are below what would otherwise be a minimum effective dose (a "sub-MED").

While the experienced clinician is able to monitor and adjust dosages for each patient relative to the severity of the headache attack and the presence of side-effects, generally available information on maximum common daily dosages of NSAIDs is useful as a cautionary guideline. Maximum daily dosages in milligrams are as follows: flurbiprofen 300; ketoprofen 300; naproxen 1500, naproxen sodium 1375; oxaprozin 1800; etodolac 1200; indomethacin 150 to 200; ketorolac 120 mg i.m. and 40 oral; nabumetone 2000; mefenamic acid 1000; and piroxicam 20. In particular instances, however, exceeding these "maximum" doses is the therapeutic choice of the medical professional.

The enhanced therapeutic effect observed for the present invention is typically achievable with sub-MED doses of one or both therapeutic agents, thereby resulting in a reduced incidence of side effects. For example, combining ergotamine tartrate 0.5 mg (instead of the standard dose of 1–3 mg) with 125–550 mg naproxen sodium will, in some instances, provide headache relief with a lower incidence of adverse events such as cardiovascular complications, nausea, or ergotism. Another example is the combination of sumatriptan 5–15 mg (instead of the usual minimum recommended dose of 25–100 mg) plus naproxen sodium 125–550 mg. In this example, the therapeutic effect is excellent and is accompanied by lower incidence of adverse events such as cardiovascular complications, weakness, tingling, warm and hot sensations, and chest discomfort. A third example is the use of sumatriptan injection 1–4 mg (instead of 6 mg which is the commonly recommended dose) combined with a suitable dose of naproxen sodium, either orally or by another route. In this instance, a significant reduction in sumatriptan side effects such as, but not limited to, tingling, weakness, flushing, asthenia, chest and upper body pressure and discomfort and the risk of cardiovascular complications is accompanied by excellent and long-lasting relief similar or superior to what one normally achieves with the 6 mg injection.

EXAMPLES

Example 1

An adult female migraineur complains of a migraine attack consisting of typical migraine headache, nausea and sensitivity to light and sound. She is dosed with a single oral tablet containing sumatriptan 25 mg and naproxen sodium 550 mg. Her symptoms start to diminish within one hour and by three hours she is completely symptom free. No relapse over the next 48 hours is reported. Her pain is relieved more quickly and with longer uninterrupted relief then when she takes either agent alone.

Example 2

An adult female migraineur is complaining of a migraine attack consisting of typical migraine headache, nausea and sensitivity to light and sound. She is dosed with a single subcutaneous injection of sumatriptan 6 mg and at the same time orally ingests a tablet containing naproxen sodium 550 mg. Her symptoms start to diminish within 20 minutes and by two hours she is completely symptom free and has no relapse over the next 24 hours. Her pain is relieved more quickly and with longer uninterrupted relief than when she takes either agent alone.

Example 3

An adult female migraineur complains of a migraine attack consisting of typical migraine headache, nausea and sensitivity to light and sound. She is dosed with a single oral tablet containing 12.5 mg sumatriptan and 550 mg naproxen sodium. Her symptoms start to diminish within one hour. By three hours she is completely symptom free and has no relapse over the next 48 hours. Her pain is relieved more quickly and with longer uninterrupted relief than when she takes either agent alone. She experiences fewer adverse sumatriptan drug reactions than if she received standard (higher) doses of sumatriptan, with particular reference to asthenia and flushing.

Example 4

An adult female migraineur, with a history of relapse headache in 6 to 24 hours when dosed with 6 mg sumatriptan alone, complains of a migraine attack consisting of typical migraine headache, nausea and sensitivity to light and sound. She is dosed with a single subcutaneous injection of 2 mg sumatriptan and orally ingests a tablet containing 550 mg naproxen sodium. Her symptoms start to diminish within 30 minutes and by two hours she is completely symptom free and has no relapse over the next 48 hours. She experiences fewer adverse sumatriptan drug reactions than if she received standard (higher) doses of sumatriptan, with particular reference to asthenia and flushing, chest discomfort, as compared reaction to with sumatriptan 6 mg injections.

Example 5

A male 25 years of age offers the same presenting history and indication as in Example 1. Treatment is by means of a single oral tablet containing 50 mg sumatriptan and 550 mg naproxen. The same result as in Example 1 is obtained.

Example 6

A variety of combinations of 5-HT agonists and NSAIDs can be made into a single dosage form, either tablet, capsule, suppository, parenteral or other. As an example, a rapidly dissolving tablet of 0.5 mg ergotamine tartrate combined with 550 mg naproxen sodium is conveniently available for use. Another example includes a rapidly dissolving tablet of 12.5 mg of sumatriptan combined with 550 mg of naproxen sodium. Other agents may also be present such as: pregelatinized maze starch, polyvinyl-pyrrolidone or hydroxypropyl methylcellulose; fillers (e.g., lactose, microcrystalline cellulose or calcium phosphate); disintegrants (e.g., potato starch, croscarmellose sodium, or sodium starch glycollate); wetting agents (e.g., sodium lauryl sulphate) or other agents for tableting.

The 5-HT agonist and NSAID combined compositions can be made up of various agents listed herein. As an example, in the case of naproxen sodium and sumatriptan, several tablet strengths are available including: 12.5 mg sumatriptan/550 mg naproxen sodium; 25 mg sumatriptan/ 550 mg naproxen sodium; 12.5 mg sumatriptan/275 mg naproxen sodium; and 25 mg sumatriptan/275 naproxen sodium. Each tablet dissolves within 20 minutes to rapidly produce effective blood levels of each component.

The 5-HT agonist and NSAID combined compositions of this invention possess valuable pharmacological properties. They effect long term migraine attack relief with a substantially reduced incidence of relapse headaches. In some instances, they provide initial migraine relief with a reduced incidence of side effects, and/or greater efficacy. This effect can be demonstrated, for example, using the methods employed in the clinical studies reviewed by Plosker and McTavish (Drugs 47:622–651 (1999); Wilkinson, et al., *Cephalalgia* 15:337–357 (1995)) and Visser, et al., (*Cephalalgia* 16:264–269 (1996)).

The pharmacologically active compositions of this invention can be processed in accordance with conventional methods of Galenic pharmacy to produce medicinal agents for administration to patients, e.g., mammals including humans. The compositions, individually or in combination, are employed in admixture with conventional excipients, i.e., pharmaceutically acceptable organic or inorganic carrier substances suitable for parenteral, enteral (e.g., oral or intranasal) or topical application which do not deleteriously react with the active compositions. Suitable pharmaceutically acceptable carriers include but are not limited to water, salt solutions, alcohols, gum arabic, vegetable oils, benzyl alcohols, polyethylene glycols, gelatin, carbohydrates such as lactose, amylose or starch, magnesium sterate, talc, titanium dioxide, silicic acid, viscous paraffin, perfume oil, fatty acid esters, hydroxymethycellulose, polyvinylpyrrolidone, etc. The pharmaceutical preparations can be sterilized and, if desired, mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active agents. They can also be combined with other active agents, e.g., vitamins. In some embodiments of the present invention, dosage forms include instructions for the use of such compositions. For parenteral application, particularly suitable are injectable, sterile solutions, preferably oily or aqueous solutions, as well as suspensions, emulsions, or implants, including suppositories. Ampules, vials, and injector cartridges are convenient unit dosages.

Sustained or directed release compositions can also be formulated, e.g., liposomes or compositions in which the active component is protected with differentially degradable coatings, e.g., by microencapsulation, multiple coatings, etc. It is also possible to freeze-dry the new compositions and use the lyophilizates obtained, for example, for the preparation of products for injection.

Generally, the compositions of this invention are dispensed in unit dosage forms comprising 1–100 mg of sumatriptan or equivalent doses of other 5-HT agonists and 200–600 mg of naproxen sodium or equivalent doses of other NSAIDs in a pharmaceutically acceptable carrier per unit dosage. The actual preferred amounts of active compositions in a specific case will vary according to the specific compositions being utilized, the particular compositions formulated, the mode of application, and the particular route of administration. Dosages for a given subject can be determined using conventional considerations, e.g., by customary comparison of the differential activities of the subject compositions and of a known agent, or by means of an appropriate, conventional pharmacological protocol.

What is claimed is:

1. A method of treating a patient for migraine headache, comprising:

(a) administering a 5-HT agonist to said patient, wherein said 5-HT agonist is a triptan; and (b) administering a long-acting, non-steroidal, anti-inflammatory drug (LA-NSAID) to said patient, wherein said LA-NSAID has a pharmacokinetic half-life of at least 4 hours and a duration of action of at least 6 hours;

wherein:

(i) said 5-HT agonist and said LA-NSAID are concomitantly administered in unit dosage form; and (ii) the respective amounts of said 5-HT agonist and said LA-NSAID administered to said patient are sufficient to produce longer lasting efficacy compared to the administration of said 5-HT agonist in the absence of said LA-NSAID or the administration of said LA-NSAID in the absence of said 5-HT agonist.

2. The method of claim 1, wherein said 5-HT agonist and said LA-NSAID are administered after the onset of symptoms associated with migraine headache.

3. A pharmaceutical composition in unit dosage form, useful in treating a migraine headache patient, which comprises:

(a) a 5-HT agonist, wherein said 5-HT agonist is a triptan; and (b) a long-acting, non-steroidal, anti-inflammatory drug (LA-NSAID), wherein said LA-NSAID has a pharmacokinetic half-life of at least 4 hours and a duration of action of at least 6 hours;

wherein the respective amounts of said 5-HT agonist and said LA-NSAID in said composition are effective, upon concomitant administration to said patient of one or more of said unit dosage forms of said composition, to produce longer lasting efficacy compared to the administration of said 5-HT agonist in the absence of said LA-NSAID or the administration of said LA-NSAID in the absence of said 5-HT agonist.

4. A therapeutic package for dispensing to, or for use in dispensing to, a migraine headache patient, which comprises:

(a) one or more unit dosage forms, each unit dosage form comprising:

(i) a 5-HT agonist, wherein said 5-HT agonist is a triptan; and (ii) a long-acting, non-steroidal, anti-inflammatory drug (LA-NSAID), wherein said LA-NSAID has a pharmacokinetic half-life of at least 4 hours and a duration of action of at least 6 hours;

wherein the respective amounts of said 5-HT agonist and said LA-NSAID in said unit dosage f6 rms are effective, upon concomitant administration to said patient of one or more of said unit dosage forms, to produce longer lasting efficacy compared to the administration of said 5-HT agonist in the absence of said LA-NSAID or the administration of said LA-NSAID in the absence of said 5-HT agonist; and (b) a finished pharmaceutical container therefore, said container containing said unit dosage form or unit dosage forms, and further comprising labeling directing the use of said package in the treatment of migraine headache.

5. A method for producing longer lasting efficacy in a migraine headache patient which comprises:
(a) administering a 5-HT agonist to said patient, wherein said 5-HT agonist is a triptan; and
(b) administering a long-acting, non-steroidal, anti-inflammatory drug (LA-NSAID) to said patient, wherein said LA-NSAID has a pharmacokinetic half-life of at least 4 hours and a duration of action of at least 6 hours; wherein:
(i) said 5-HT agonist and said LA-NSAID are concomitantly administered in unit dosage form after the onset of symptoms associated with migraine headache; and
(ii) the respective amounts of said 5-HT agonist and said LA-NSAID administered to said patient are effective to produce longer lasting efficacy compared to the administration of said 5-HT agonist in the absence of said LA-NSAID or the administration of said LA-NSAID in the absence of said 5-HT agonist.

6. The method or composition of any one of claims 1–5, wherein said 5-HT agonist is sumatriptan.

7. The method or composition of any one of claims 1–5, wherein said 5-HT agonist is sumatriptan non-parenterally administered in an amount of from about 25 to 100 mg.

8. The method or composition of any one of claims 1–5, wherein said 5-HT agonist and said said LA-NSAID are administered orally, intranasally, rectally, or sublingually.

9. The method or composition of any one of claims 1–5, wherein said 5-HT agonist is sumatriptan administered parenterally in an amount of about 6 mg.

10. The method or composition of any one of claims 1–5, wherein said LA-NSAID is naproxen or a pharmaceutically acceptable salt thereof.

11. The method or composition of any one of claims 1–5, wherein said LA-NSAID is naproxen or a pharmaceutically acceptable salt in an amount of greater than 200 mg.

12. The method or composition of any one of claims 1–5, wherein said 5-HT agonist is sumatriptan, and said LA-NSAID is naproxen in an oral unit dosage form comprising sumatriptan in an amount of greater than 25 mg and naproxen in an amount of greater than 200 mg.

13. The method or composition of any one of claims 1–5, wherein said concomitant administration comprises the co-timely and coordinated administering of a therapeutically effective amount of at least one additional analgesic.

14. The method or composition of any one of claims 1–5, wherein said 5-HT agonist is selected from the group consisting of sumatriptan, eletriptan, rizatriptan, frovatriptan, almotriptan, zolmitriptan and naratriptan.

15. The method or composition of claim 14, wherein said 5-HT agonist is sumatriptan.

16. The method or composition of claim 14, wherein said 5-HT agonist is eletriptan.

17. The method or composition of claim 14, wherein said 5-HT agonist is rizatriptan.

18. The method or composition of claim 14, wherein said 5-HT agonist is frovatriptan.

19. The method or composition of claim 14, wherein said 5-HT agonist is almotriptan.

20. The method or composition of claim 14, wherein said 5-HT agonist is zolmitriptan.

21. The method or composition of claim 14, wherein said 5 HT agonist is naratriptan.

22. The method or composition of any one of claims 1–5, wherein said LA-NSAID is selected from the group consisting of flurbiprofen, ketoprofen, naproxen, oxaprozin, etodolac, indomethacin, ketorolac, nabumetone, mefanamic acid, and piroxicam.

23. The method or composition of claim 22, wherein said LA-NSAID is naproxen.

24. The method or composition of claim 23, wherein said naproxen is in the form of a sodium salt.

25. A pharmaceutical composition In unit dosage form, useful in treating a migraine headache patient, wherein the active agents in said pharmaceutical composition consist essentially of:
(a) a 5-HT agonist, wherein said 5-HT agonist is a triptan; and
(b) a long-acting, non-steroidal, anti-inflammatory drug (LA-NSAID), wherein said LA-NSAID has a pharmacokinetic half-life of at least 4 hours and a duration of action of at least 6 hours;
wherein the respective amounts of said 5-HT agonist and said LA-NSAID in said composition are effective, upon concomitant administration to said patient of one or more of said unit dosage forms of said composition, to produce longer lasting efficacy compared to the administration of said 5-HT agonist in the absence of said LA-NSAID or the administration of said LA-NSAID in the absence of said 5-HT agonist.

26. The pharmaceutical composition of claim 25, wherein said 5-HT agonist is sumatriptan and said LA-NSAID is naproxen.

27. The pharmaceutical composition of claim 26, wherein:
a) said pharmaceutical composition is suitable for oral administration;
b) said sumatriptan is present in an amount of between 25 and 100 mg; and
c) said naproxen is present in an amount of between 200 and 600 mg.

28. A pharmaceutical composition in unit dosage form, useful in treating a migraine headache patient, wherein the active agents in said pharmaceutical composition consist of:
(a) a 5-HT agonist, wherein said 5-HT agonist is a triptan; and
(b) a long-acting, non-steroidal, anti-inflammatory drug (LA-NSAID), wherein said LA-NSAID has a pharmacokinetic half-life of at least 4 hours and a duration of action of at least 6 hours;
wherein the respective amounts of said 5-HT agonist and said LA-NSAID in said composition are effective, upon concomitant administration to said patient of one or more of said unit dosage forms of said composition, to produce longer lasting efficacy compared to the administration of said 5-HT agonist in the absence of said LA-NSAID or the administration of said LA-NSAID in the absence of said 5-HT agonist.

29. The pharmaceutical composition of claim 28, wherein said 5-HT agonist is sumatriptan and said LA-NSAID is naproxen.

30. The pharmaceutical composition of claim 29, wherein:
a) said pharmaceutical composition is suitable for oral administration;
b) said sumatriptan is present in an amount of between 25 and 100 mg; and
c) said naproxen is present in an amount of between 200 and 600 mg.

31. A method of treating a patient for migraine headache, comprising administering the pharmaceutical composition of any one of claims 25–30 to said patient after the onset of symptoms associated with migraine headache.

32. A therapeutic package for dispensing to, or for use in dispensing to, a migraine headache patient, which comprises:

(a) the pharmaceutical composition in unit dosage form of any one of claims 25–30: and (b) a finished pharmaceutical container therefore, said container containing said unit dosage form or unit dosage forms, and further comprising labeling directing the use of said pharmaceutical composition in the treatment of migraine headache.

* * * * *

UNITED STATES PATENT AND TRADEMARK OFFICE
CERTIFICATE OF CORRECTION

PATENT NO. : 6,586,458 B1
APPLICATION NO. : 09/559753
DATED : July 1, 2003
INVENTOR(S) : John Plachetka It is certified that error appears in the above-identified patent and that said Letters Patent is hereby corrected as shown below:

On the Title page, the section entitled "Related U.S. Application Data" should be revised to clarify that the issued patent, i.e., US 6,586,458, is a continuation-in-part of US 09/253,278. Thus, the phrase referring to US 09/253,278 should be moved from the end of the section to the beginning. The words "which is" should no longer precede the phrase and the words "now abandoned" should be placed in parentheses. The corrected paragraph should read as follows:

-- Related U.S. Application Data
(63) Continuation-in-part of application No. 09/253,278, filed Feb. 19, 1999 (now abandoned), and a continuation-in-part of application No. 09/151,912, filed on Sep. 11, 1998, now Pat. No. 6,060,499, which is a division of application No. 08/907,826, filed on Aug. 14, 1997, now Pat. No. 5,872,145. --

In column 1, beginning on line 7, the paragraph after "Cross Reference to Related Applications" should also be corrected to clarify that the issued patent is a continuation-in-part of US 09/253,278. The phrase referring to 09/253,278 should be removed from the end of the paragraph and placed in the first sentence. The abbreviation CIP should be replaced with "continuation in part" and the words "now abandoned" should be placed within parentheses. The corrected paragraph should read as follows:

UNITED STATES PATENT AND TRADEMARK OFFICE
CERTIFICATE OF CORRECTION

PATENT NO.        : 6,586,458 B1
APPLICATION NO.   : 09/559753
DATED             : July 1, 2003
INVENTOR(S)       : John Plachetka It is certified that error appears in the above-identified patent and that said Letters Patent is hereby corrected as shown below:

-- The present application is a continuation-in-part of U.S. Ser. No. 09/253,278, filed Feb. 19, 1999 (now abandoned), and a continuation-in-part of U.S. Ser. No. 09/151,912, filed Sep. 11, 1998 now U.S. Pat. No. 6,060,499. The '912 application is a division of U.S. Ser. No. 08/907,826, filed Aug. 14, 1997 (now U.S. Pat. No. 5,872,145) which claims priority to U.S. provisional application No. 60/024,129, filed Aug. 16, 1996 (now abandoned). --

Signed and Sealed this

Seventeenth Day of June, 2008

JON W. DUDAS
*Director of the United States Patent and Trademark Office*